(12) United States Patent
Hedvati et al.

(10) Patent No.: US 7,462,738 B2
(45) Date of Patent: Dec. 9, 2008

(54) PROCESSES FOR THE PREPARATION OF R-(+)-3-(CARBAMOYL METHYL)-5-METHYLHEXANOIC ACID AND SALTS THEREOF

(75) Inventors: Lilach Hedvati, Doar Ha Hefer (IL); Eyal Gilboa, Bat-Yam (IL); Sharon Avhar-Maydan, Givataym (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/807,098

(22) Filed: May 24, 2007

(65) Prior Publication Data

US 2007/0293694 A1 Dec. 20, 2007

Related U.S. Application Data

(60) Provisional application No. 60/808,320, filed on May 24, 2006, provisional application No. 60/814,245, filed on Jun. 15, 2006, provisional application No. 60/843,817, filed on Sep. 11, 2006, provisional application No. 60/850,868, filed on Oct. 10, 2006, provisional application No. 60/918,177, filed on Mar. 14, 2007, provisional application No. 60/920,348, filed on Mar. 26, 2007.

(51) Int. Cl.
C07C 229/00 (2006.01)
(52) U.S. Cl. .................................................. 562/553
(58) Field of Classification Search ........................ None
See application file for complete search history.

(56) References Cited

U.S. PATENT DOCUMENTS

| | | | |
|---|---|---|---|
| 5,010,189 | A | 4/1991 | Herold et al. |
| 5,599,973 | A | 2/1997 | Silverman et al. |
| 5,616,793 | A | 4/1997 | Huckabee et al. |
| 5,629,447 | A | 5/1997 | Huckabee et al. |
| 5,637,737 | A | 6/1997 | Andres et al. |
| 5,637,767 | A | 6/1997 | Grote et al. |
| 6,001,876 | A | 12/1999 | Singh |
| 6,197,819 | B1 | 3/2001 | Silverman et al. |
| 6,333,198 | B1 | 12/2001 | Edmeades et al. |
| 6,488,964 | B2 | 12/2002 | Bruna et al. |
| 6,580,003 | B2 | 6/2003 | Deng et al. |
| 6,891,059 | B2 | 5/2005 | Burk et al. |
| 6,924,377 | B2 | 8/2005 | Blazecka et al. |
| 7,141,695 | B2 | 11/2006 | Przewosny et al. |
| 2001/0016665 | A1 | 8/2001 | Grote et al. |
| 2003/0225149 | A1 | 12/2003 | Blazecka et al. |
| 2005/0222464 | A1 | 10/2005 | Hoge, II |
| 2005/0228190 | A1 | 10/2005 | Bao et al. |
| 2005/0283023 | A1 | 12/2005 | Hu et al. |
| 2006/0270871 | A1 | 11/2006 | Khanduri et al. |
| 2007/0073085 | A1 | 3/2007 | Hedvati et al. |
| 2008/0014280 | A1 | 1/2008 | Kumar et al. |

FOREIGN PATENT DOCUMENTS

| | | |
|---|---|---|
| CN | 1 634 869 | 7/2005 |
| CZ | 297 970 | 3/2007 |
| WO | WO 96/38405 A1 | 12/1996 |
| WO | WO 96/40617 A1 | 12/1996 |
| WO | WO 01/55090 A1 | 8/2001 |
| WO | WO 2005/100580 | 10/2005 |
| WO | WO 2006/000904 A2 | 1/2006 |
| WO | WO 2006/136087 | 12/2006 |
| WO | WO 2008/004044 | 1/2008 |
| WO | WO 2008/007145 | 1/2008 |
| WO | WO 2008/009897 | 1/2008 |

OTHER PUBLICATIONS

Andruszkiewicz and Silverman, "A Convenient Synthesis of 3-Alkyl-4-Aminobutanoic Acids," *Synthesis*, 953-955 (1989).
Barnes, D.M., et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram," *J. Am. Chem. Soc.*, 124(44): 13097-13105 (2002).
Berner et al. "Asymmetric Michael Additions to Nitroalkenes," *European Journal of Organic Chemistry*, 1877-1894 (2002).
Cason, J. et al., "Branched-Chain Fatty Acids. XXVII. Further Study of the Dependence of Rate of Amide Hydrolysis on Substitution near the Amide Group. Relative Rates of Hydrolysis of Nitrile to Amide and Amide to Acid," *J. Org. Chem.*, 18(9): 1129-1136 (1953).
Chen, AO et al., "Synthesis of Pregabalin," *Zhongguo YiYao Gongye Zazhi*, 35(4): 195-196 (2004).
Colonge et al., "Preparation De Pyrrolidones-2 et de Gamma-Aminoacides," *Bulletin De La Societe Chimique De France, Societe Francaise De Chimie*, 598-603 (1962).
Day and Thorpe, "The Formation and Reactions of Imino-compounds. Part XX. The Condensation of Aldehydes with Cyanoacetamide," *J. Chem. Soc.*, 117: 1465-1474 (1920).
Hoekstra, M.S. et al., "Chemical Development of CI-1008, an Enantiomerically Pure Anticonvulsant," *Organic Process Research and Development*, 1(1): 26-38 (1997).
Karanewsky, D.S. et al., "Practical Synthesis of an Enantiomerically Pure Synthon for the Preparation of Mevinic Acid Analogues," *J. Org. Chem.*, 56(11): 3744-3747 (1991).
Li, H. et al., "Highly Enantioselective Catalytic Conjugate Addition of Malonate and β-Ketoester to Nitroalkenes: Asymmetric C-C Bond Formation with New Bifunctional Organic Catalysts Based on Cinchona Alkaloids," *J. Am. Chem. Soc.*, 126(32): 9906-9907 (2004).
Martin, L. et al., "Pregabalin," *Drugs of the Future*, 24(8): 862-870 (1999).

(Continued)

*Primary Examiner*—Paul A Zucker
(74) *Attorney, Agent, or Firm*—Kenyon & Kenyon LLP

(57) ABSTRACT

Provided are processes for the synthesis of R-(+)-3-(carbamoylmethyl)-5-methylhexanoic acid and salts thereof, intermediates in the synthesis of S-pregabalin.

81 Claims, No Drawings

OTHER PUBLICATIONS

Okino, T. et al., "Enantio- and Diastereoselective Michael Reaction of 1,3-Dicarbonyl Compounds to Nitroolefins Catalyzed by a Bifunctional Thiourea," *J. Am. Chem. Soc.*, 127(1): 119-125 (2005).

Sammis, G.M. et al., "Highly Enantioselective Catalytic Conjugate Addition of Cyanide to α,β-Unsaturated Imides", *J. Am. Chem. Soc.*, 125(15): 4442-43 (2003).

Shintani, Ryo et al., "Highly Enantioselective Desymmetrization of Anhydrides by Carbon Nucleophiles: Reactions of Grignard Reagents in the Presence of (-)-Sparteine," *Angewandte Chemie, International Edition*, 41(6): 1057-1059 (2002).

Snyder et al., Introduction to Modern Liquid Chromatography, 549-572 (2d ed., John Wiley & Sons, 1979).

Strobel et al., Chemical Instrumentation: A Systematic Approach, 391-393, 879-894, 922-925, 953 (3d ed. 1989).

Theisen, P.D. et al., "Prochiral Recognition in the Reaction of 3-Substituted Glutaric Anhydrides with Chiral Secondary Alcohols," *J. Org. Chem.*, 58(1): 142-146 (1993).

Verma, Rekha et al., "Desymmetrization of prochiral anhydrides with Evans' oxazolidinones: an efficient route to homochiral glutaric and adipic acid derivatives," *J. Chem. Soc., Perkin Transactions 1: Organic and Bio-Organic Chemistry*, 257-264 (1999).

Yamamoto et al., "Stereoselective Synthesis of (E)-Alkylidenesuccinates by Palladium-catalyzed Carbonylation," *Bull. Chem. Soc. Japan*, 58(11): 3397-3398 (1985).

International Search Report and Written Opinion of ISA from corresponding International Patent Application No. PCT/US2007/012485 dated Feb. 26, 2008.

Hiratake et al., "Enantiotopic-group Differentiation. Catalytic Asymmetric Ring-opening of Prochiral Cyclic Acid Anhydrides with Methanol, using Cinchona Alkaloids", *Journal of the Chemical Society*, Perkins Trans. 1, 1053-1058 (1987).

PROCESSES FOR THE PREPARATION OF R-(+)-3-(CARBAMOYL METHYL)-5-METHYLHEXANOIC ACID AND SALTS THEREOF

CROSS-REFERENCE TO RELATED APPLICATIONS

This application claims the benefit of priority to U.S. provisional application Ser. Nos. 60/808,320, filed May 24, 2006; 60/814,245, filed Jun. 15, 2006; 60/843,817, filed Sep. 11, 2006; 60/850,868, filed Oct. 10, 2006; 60/918,177, filed Mar. 14, 2007; and 60/920,348, filed Mar. 26, 2007, hereby incorporated by reference.

FIELD OF THE INVENTION

The invention encompasses processes for the synthesis of R-(+)-3-(carbamoylmethyl)-5-methylhexanoic acid ("R-CMH") and salts thereof, intermediates in the synthesis of S-pregabalin.

BACKGROUND OF THE INVENTION (S)-Pregabalin, (S)-(+)-3-(aminomethyl)-5-methylhexanoic acid, a compound having the chemical structure,

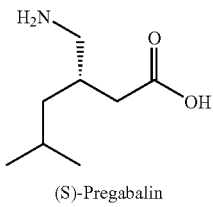

(S)-Pregabalin is a γ-amino butyric acid or (S)-3-isobutyl (GABA) analogue. (S)-Pregabalin has been found to activate GAD (L-glutamic acid decarboxylase). (S)-Pregabalin has a dose dependent protective effect on-seizure, and is a CNS-active compound. (S)-Pregabalin is useful in anticonvulsant therapy, due to its activation of GAD, promoting the production of GABA, one of the brain's major inhibitory neurotransmitters, which is released at 30 percent of the brains synapses. (S)-Pregabalin has analgesic, anticonvulsant, and anxiolytic activity.

Preparation of (S)-Pregabalin, as Disclosed in U.S. Pat. No. 5,616,793, and in DRUGS OF THE FUTURE, 24 (8), 862-870 (1999) is performed by obtaining the intermediate, 3-(carbamoylmethyl)-5-methylhexanoic acid ("CMH"), which is then optically resolved to give R-CMH, which is then converted to (S)-Pregabalin, as described in the following scheme:

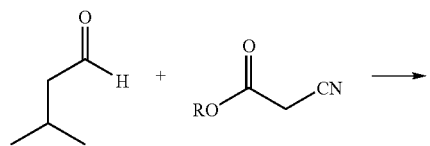

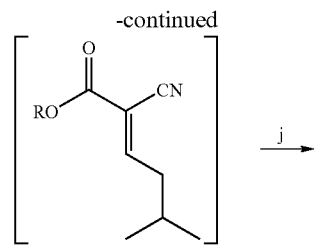

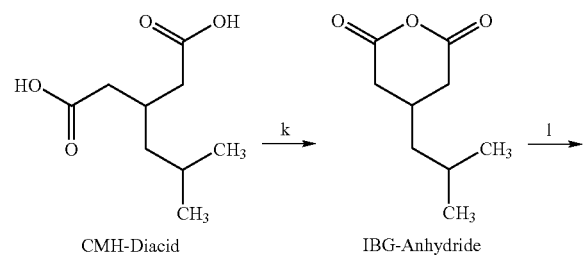

CMH-Diacid     IBG-Anhydride

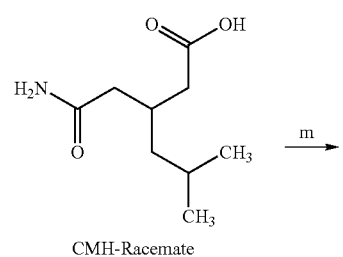

CMH-Racemate

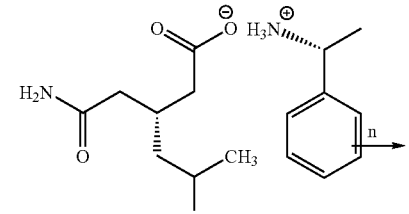

R-CMH:PEA salt

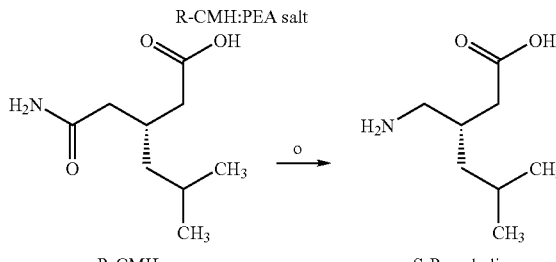

R-CMH     S-Pregabalin j: 1) Dialkyl malonate, 2) HCl, H$_2$O
k: Ac$_2$O
l: 1) NH$_3$ (aq), MTBE, 2) HCl
m: EtOH/CHCl$_3$
n: HCl/H$_2$O
o: 1) NaOH, Br$_2$, 2)HCl There is a need in the art for additional processes for preparing R-CMH and salts thereof.

SUMMARY OF THE INVENTION

In one embodiment, the invention encompasses a process for preparing (R)-(+)-3-(carbamoylmethyl)-5-methylhexanoic acid or a salt thereof having the formula

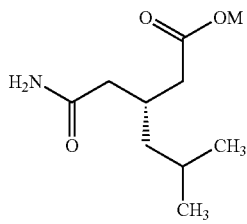

comprising: a) asymmetrically ring opening 3-isobutylglutaric anhydride to obtain a chiral ester having the formula

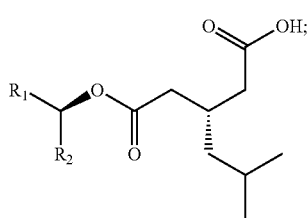

b) amidating the chiral ester to obtain a (R)-(+)-3-(carbamoylmethyl)-5-methylhexanoic acid salt having the formula

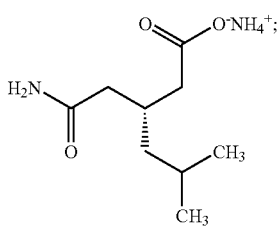

and, optionally, c) converting the (R)-(+)-3-(carbamoylmethyl)-5-methylhexanoic acid salt to (R)-3-(carbamoylmethyl)-5-methylhexanoic acid, wherein $R_1$ and $R_2$ are independently selected from the group consisting of H, aliphatic, branched or cyclic $C_1$ to $C_{12}$ hydrocarbyl, $C_6$ to $C_9$ aromatic hydrocarbyl and $CO_2H$, and M is either H or $NH_4^+$.

In another embodiment, the invention encompasses a process for preparing R-(+)-3-(carbamoylmethyl)-5-methylhexanoic acid or a salt thereof having the formula

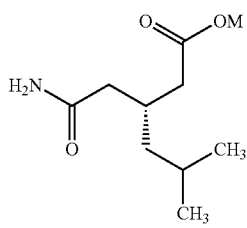

comprising: a) combining 3-isobutylglutaric anhydride, a chiral alcohol, a solvent selected from the group consisting of $C_{6-10}$ aromatic hydrocarbons, $C_{3-5}$ ketones, $C_{2-5}$ ethers, $C_{2-7}$ esters, $C_{1-2}$ halogenated hydrocarbons, and $C_{1-4}$ nitriles, and a base to obtain a chiral ester of the formula

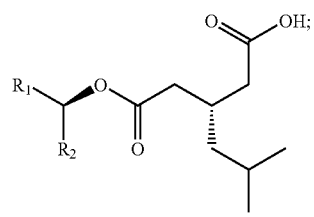

b) mixing with ammonia to obtain a (R)-(+)-3-(carbamoylmethyl)-5-methylhexanoic acid salt having the formula

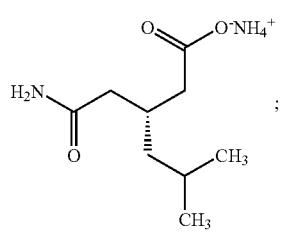

; and, optionally, c) adding an acid to obtain R-(+)-3-(carbamoylmethyl)-5-methylhexanoic acid, wherein $R_1$ and $R_2$ are independently selected from the group consisting of H, aliphatic, branched, or cyclic $C_{1-12}$ hydrocarbons, $C_{6-9}$ aromatic hydrocarbons, and $CO_2H$; and M is either H or $NH_4^+$.

In another embodiment, the invention encompasses a process for preparing R-(+)-3-(carbamoylmethyl)-5-methylhexanoic acid or a salt thereof having the formula

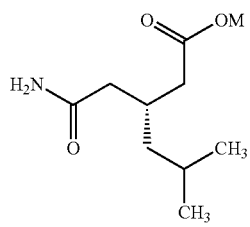

comprising: a) combining 3-isobutylglutaric anhydride, a non-chiral alcohol, a chiral amine, and a solvent selected from the group consisting of $C_{6-10}$ aromatic hydrocarbons, $C_{2-5}$ ethers, $C_{1-2}$ halogenated hydrocarbons, and mixtures thereof to obtain a chiral ester of the formula

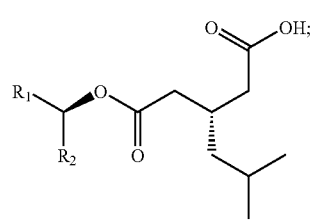

b) mixing with ammonia to obtain a (R)-(+)-3-(carbamoylmethyl)-5-methylhexanoic acid salt having the formula

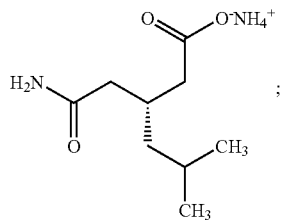

and, optionally, c) adding an acid to obtain R-(−)-3-(carbamoylmethyl)-5-methylhexanoic acid, wherein $R_1$ and $R_2$ are independently selected from the group consisting of H, aliphatic, branched, or cyclic $C_{1-12}$ hydrocarbons, $C_{6-9}$ aromatic hydrocarbons, and $CO_2H$; and M is either H or $NH_4^+$.

In another embodiment, the invention encompasses a process for preparing R-(+)-3-(carbamoylmethyl)-5-methylhexanoic acid or a salt thereof having the formula

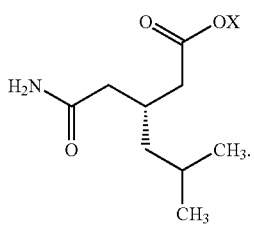

comprising: a) combining a chiral ester having the formula

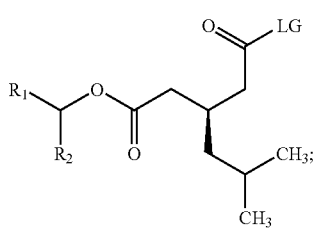

with an acid activating agent to form an activated acid derivative having the formula

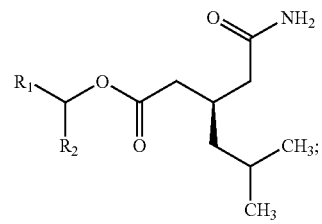

b) amidating the activated acid derivative to obtain a carbamoyl ester having the formula c) hydrolyzing the carbamoyl ester with an acid or a base to obtain R-(+)-3-(carbamoylmethyl)-5-methylhexanoic acid or a salt thereof, respectively; and, optionally, d) converting the salt of R-(+)-3-(carbamoylmethyl)-5-methylhexanoic acid into R-(+)-3-(carbamoylmethyl)-5-methylhexanoic acid, wherein $R_1$ and $R_2$ are independently selected from the group consisting of H, aliphatic, branched, or cyclic $C_{1-12}$ hydrocarbons, $C_{6-9}$ aromatic hydrocarbons, and $CO_2H$; and LG is a leaving group; where the leaving group is derived from the acid activating agent; and wherein X is H or an alkali metal.

In another embodiment, the invention encompasses a process for preparing (S)-pregabalin comprising preparing R-(+)-3-(carbamoylmethyl)-5-methylhexanoic acid or salts thereof by any of the above-described processes, and converting the R-(+)-3-(carbamoylmethyl)-5-methylhexanoic acid or salts thereof into (S)-pregabalin.

DETAILED DESCRIPTION OF THE INVENTION

The invention encompasses processes for the preparation of R-CMH, in high yields, without resolving the CMH racemate, as disclosed in the prior art and therefore, avoiding the resolution and the recovery of the undesired enantiomer. In addition, the processes can be adapted easily to an industrial scale.

In one embodiment, the invention encompasses a process for preparing R-CMH or a salt thereof that may be illustrated by the following Scheme 1.

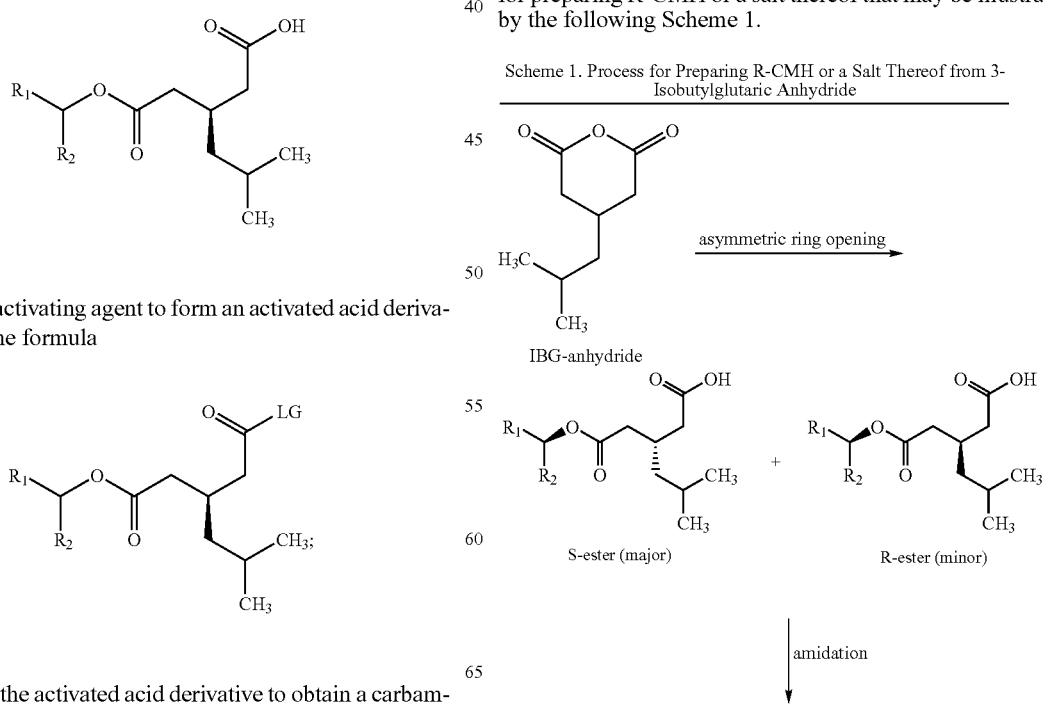

Scheme 1. Process for Preparing R-CMH or a Salt Thereof from 3-Isobutylglutaric Anhydride

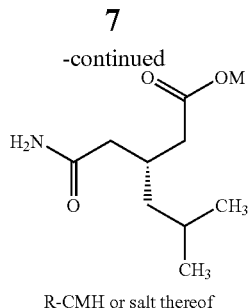

R-CMH or salt thereof wherein $R_1$ and $R_2$ are independently selected from the group consisting of H, aliphatic, branched, or cyclic $C_{1-12}$ hydrocarbons, $C_{6-9}$ aromatic hydrocarbons, and $CO_2H$; and M is either H or $NH_4^+$. Preferably, $R_1$ is $CO_2H$ or H; $R_2$ is H, a $C_{6-9}$ aromatic hydrocarbon, or an aliphatic or branched $C_{1-12}$ hydrocarbon; or $R_1$ and $R_2$ form together a cyclic $C_{1-12}$ hydrocarbon.

Preferably, the $C_{6-9}$ aromatic hydrocarbon is phenyl. Preferably, the aliphatic or branched $C_{1-12}$ hydrocarbon is methyl. Preferably, the cyclic $C_{1-12}$ hydrocarbon is 1,3,3-trimethylbicyclo[2.2.1]heptane. Preferred combinations of $R_1$ and $R_2$ are $CO_2H$ and phenyl, H and H, H and Me, H and phenyl, respectively, or $R_1$ and $R_2$ form together 1,3,3-trimethylbicyclo[2.2.1]heptane of the following formula

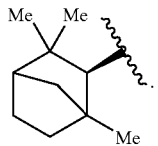

The asymmetric ring opening step may be accomplished with either (i) a chiral alcohol, or (ii) with a non-chiral alcohol in combination with a chiral amine, which acts as a chiral inductor.

When a chiral alcohol is used, the asymmetric ring opening step typically comprises combining 3-isobutylglutaric anhydride ("IBG-anhydride"), a chiral alcohol S-ester, a solvent selected from the group consisting of $C_{6-10}$ aromatic hydrocarbons, $C_{3-5}$ ketones, $C_{2-5}$ ethers, $C_{2-7}$ esters, $C_{1-2}$ halogenated hydrocarbons, and $C_{1-4}$ nitriles, and a base.

Preferably, the base is selected from the group consisting of sodium hydride ("NaH") and butyl lithium ("BuLi"). More preferably, the base is the inorganic base NaH. Preferably, the NaH is in the form of a 60% w/w suspension in oil The chiral alcohol opens IBG-anhydride in a stereospecific manner. Thus, one of ordinary skill in the art would appreciate that one enantiomer of the chiral alcohol leads to the formation of the S-ester, while the opposite enantiomer leads to the formation of the R-ester. Examples of suitable chiral alcohols include, but not limited to, (S)-fenchyl alcohol, (S)-mandelic acid, benzylmandelate, ethylmandelate, methylmandelate, 1-phenylethanol, 1-phenyl-2-propanol, 1-phenyl-1-propanol, and trifluoromethyl-benzyl alcohol. Preferably, the chiral alcohol is either (S)-fenchyl alcohol or (S)-mandelic acid.

Preferably, the $C_{6-10}$ aromatic hydrocarbon is a $C_{6-8}$ aromatic hydrocarbon, more preferably a $C_{6-7}$ aromatic hydrocarbon, and most preferably toluene. Preferably, the $C_{3-5}$ ketone is a $C_{3-4}$ ketone, more preferably a $C_3$ ketone, and most preferably acetone. A preferred $C_{2-5}$ ether is a $C_{4-5}$ ether, and a more preferred $C_{2-5}$ ether is either tetrahydrofuran ("THF"), or methyl tert-butylether ("MTBE"). Preferably, the $C_{2-7}$ ester is a $C_{2-5}$ ester, more preferably a $C_{2-4}$ ester, and most preferably a $C_4$ ester. A particularly preferred $C_{2-7}$ ester is ethyl acetate. A preferred $C_{1-2}$ halogenated hydrocarbon is a $C_1$ halogenated hydrocarbon, and a more preferred $C_{1-2}$ halogenated hydrocarbon is dichloromethane ("DCM"). Preferably, the $C_{1-4}$ nitrile is a $C_{1-2}$ nitrile, more preferably a $C_2$ nitrile, and most preferably acetonitrile ("ACN"). The most preferred solvent is toluene.

Typically, the solvent and the chiral alcohol are combined first to provide a mixture, and the base is then added to the mixture. Preferably, the inorganic base is added to the mixture at a temperature of about −78° C. to about 110° C., more preferably about −40° C. to about 40° C., and most preferably at about −20° C. to about 20° C.

After the addition of the base, IBG-anhydride is added to the mixture. The IBG-anhydride can be provided neat or in the form of a solution. When provided in the form of a solution, the solvent is as described above. The IBG-anhydride may be added drop-wise. When the anhydride is added drop-wise, the addition is preferably done over a period of about 0.5 hour to about 3 hours, more preferably about 0.5 hour to about 1 hour.

After the addition of the IBG-anhydride, the mixture is preferably maintained at a temperature of about 0° C. to about 50° C., and more preferably about 20° C. to about 30° C., to obtain the S-ester having the following structure.

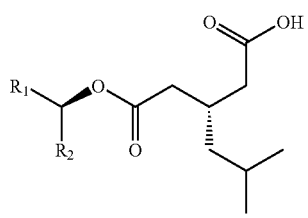

Preferably, the mixture is maintained for about 1 to about 6 hours, and more preferably for about 3 hours.

When a non-chiral alcohol in combination with a chiral amine is used, the asymmetric ring opening step typically comprises combining IBG-anhydride, a chiral amine, a non-chiral alcohol, and a solvent selected from the group consisting of $C_{6-10}$ aromatic hydrocarbons, $C_{2-5}$ ethers, $C_{1-2}$ halogenated hydrocarbons, and mixtures thereof.

Preferably, the $C_{6-10}$ aromatic hydrocarbon is a $C_{6-8}$ aromatic hydrocarbon, more preferably a $C_{6-7}$ aromatic hydrocarbon, and most preferably toluene. A preferred $C_{2-5}$ ether is a $C_{4-5}$ ether and a more preferred $C_{2-5}$ ether is THF. A preferred $C_{1-2}$ halogenated hydrocarbon is a $C_1$ halogenated hydrocarbon and a more preferred $C_{1-2}$ halogenated hydrocarbon is DCM. The most preferred solvent is toluene.

The chiral amine serves as a chiral inductor for the non-chiral alcohol, thereby leading to a stereospecific opening of IBG-anhydride. Thus, one of ordinary skill in the art would appreciate that one enantiomer of the chiral amine leads to the formation of the S-ester, while the opposite enantiomer leads to the formation of the R-ester. Preferably, the chiral amine is a chiral alkaloid. Preferably, the chiral alkaloid is a cinchona alkaloid. Examples of suitable cinchona alkaloids include, but are not limited to, quinidine, cinchonine and their dehydro derivatives. Preferably, the chiral amine is quinidine of the following structure:

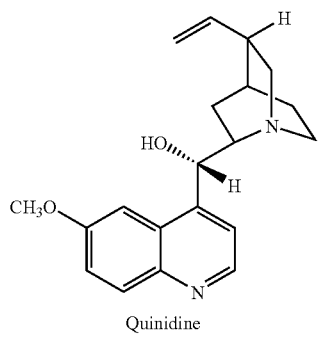

Quinidine

Preferably, the non-chiral alcohol is a $C_{1-7}$ alcohol. Preferably, the $C_{1-7}$ alcohol is methanol, ethanol, propanol, n-butanol, and benzyl alcohol. More preferably, the $C_{1-7}$ alcohol is methanol.

Typically, the non-chiral alcohol is added to a suspension of the IBG-anhydride and the chiral amine in a solvent selected from the group consisting of $C_{6-10}$ aromatic hydrocarbons, $C_{2-5}$ ethers, $C_{1-2}$ halogenated hydrocarbons, and mixtures thereof. Preferably, the alcohol is added to the suspension at a temperature of about 20° C. to about −78° C., more preferably about −40° C. to about −60° C. The non-chiral alcohol may be added drop-wise to the suspension. When the addition is drop-wise, it is preferably done over a period of about 15 minutes to about 45 minutes.

Typically, the addition of the non-chiral alcohol to the suspension provides a mixture. Preferably, the mixture is stirred for about 2 to about 96 hours and more preferably for about 2 to about 24 hours, to obtain the S-ester of the following formula.

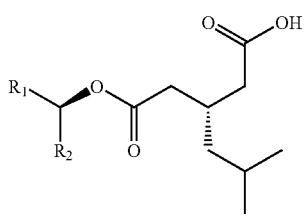

The above S-ester prepared by either of the above methods may be recovered by any method known to one of ordinary skill in the art. Such methods include, but are not limited to, removing the solvent, and optionally adding an acid, and drying.

Typically, the recovered S-ester is a mixture of two diastereomers, referred to as S-ester and R-ester of the following formulas:

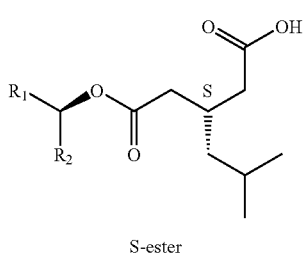

S-ester

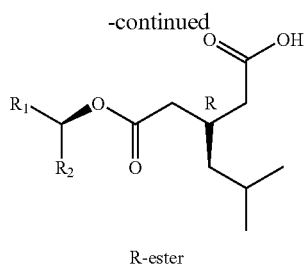

R-ester where the S-ester is the major diastereomer in the mixture. Preferably, the diastereomeric ratio is about 80:20 to about 95:5 area by HPLC, of the S-ester to the R-ester, respectively.

Optionally, the recovered mixture of diastereomers can be crystallized to increase the ratio of the S-ester to the R-ester, prior to reacting with ammonia. The crystallization comprises dissolving the mixture of diastereomers in a solvent selected from the group consisting of $C_{6-10}$ aromatic hydrocarbons, $C_{3-5}$ ketones, $C_{2-5}$ ethers, $C_{2-7}$ esters, $C_{1-2}$ halogenated hydrocarbons, $C_{1-4}$ nitriles, and mixtures thereof, and precipitating the S-ester from the solution, while the R-ester remains in solution. Preferably, the mixture of diastereomers is dissolved in a mixture of solvents. A preferred mixture of solvents is that of a $C_{6-10}$ aromatic hydrocarbon and a $C_{2-7}$ ester. More preferably, the mixture is that of toluene and ethyl acetate.

The mixture of diastereomers and solvent may optionally be heated to dissolve the mixture of diastereomers to form a solution. Preferably, the combination is heated to a temperature of about 40° C. to about 150° C., and more preferably about 60° C. to about 120° C. Typically, the obtained solution is cooled to precipitate the S-ester. Preferably, the solution is cooled to a temperature of about 30° C. to about 0° C., and more preferably about 20° C. to about 2° C. The precipitated S-ester may be recovered by filtration.

Typically, the crystallized S-ester contains less of the R-ester than the starting S-ester. Preferably, the ratio of the two diastereomers is of at least 95:5 area by HPLC of the S-ester to the R-ester, respectively.

The amidation step comprises mixing the S-ester of the chiral ester, obtained by any of the above processes, with ammonia, and optionally, followed by adding an acid. The reaction between the S-ester and ammonia leads to the R-CMH ammonium salt of the formula,

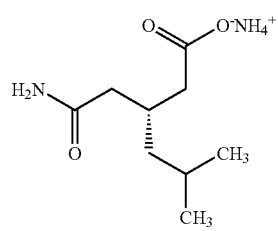

which can then be reacted with an acid to obtain R-CMH.

Preferably, the ammonia is provided in the form of a solution in a solvent selected from the group consisting of water, an organic solvent, and mixtures of water and organic solvent. Preferably, the organic solvent is selected from the group consisting of: methanol, ethanol, ethylene glycol, isopropanol, ethylacetate, and acetonitrile. The solution of ammonia can be obtained by bubbling ammonia gas into the solvent. $NH_4Cl$ may also be combined with the ammonia and the S-ester.

Preferably, the combination of the S-ester and ammonia forms a mixture, which is maintained at a temperature of about −40° C. to about 110° C., more preferably, at about 40° C. to about 110° C., and most preferably at about 40° C. to about 80° C. to obtain the ammonium salt of R-CMH. Preferably, the mixture is maintained for about 2 to about 48 hours, and more preferably for about 6 to 30 hours. Preferably, the mixture is maintained at a pressure of about 1 to about 6 atmospheres, and more preferably about 1 to about 5 atmospheres.

Preferably, the acid is selected from the group consisting of HCl, HBr, $H_2SO_4$, $H_3PO_4$, acetic acid, and formic acid. More preferably, the acid is HCl.

Preferably, the acid is present in an amount sufficient to obtain a pH of about 0 to about 5, and more preferably about 2 to about 4. After the acid is added, cooling is conducted to precipitate the R-CMH. Preferably, the cooling is to a temperature of about 10° C. to about −5° C., and more preferably to about 5° C. to about 0° C.

The R-CMH or its salt thus obtained may be recovered by any method known to one of ordinary skill in the art. Such methods include, but are not limited to, filtering, extracting the R-CMH or its salt with a solvent, evaporating the solvent and drying.

Preferably, the asymmetric ring opening and the amidation can be performed as one-pot processes, i.e., without isolation of the S-ester.

In another embodiment, the invention encompasses a process for preparing R-CMH and salts thereof that may be illustrated by the following Scheme 2.

Scheme 2. Process for Preparing R-CMH or Salts Thereof from an R-Ester

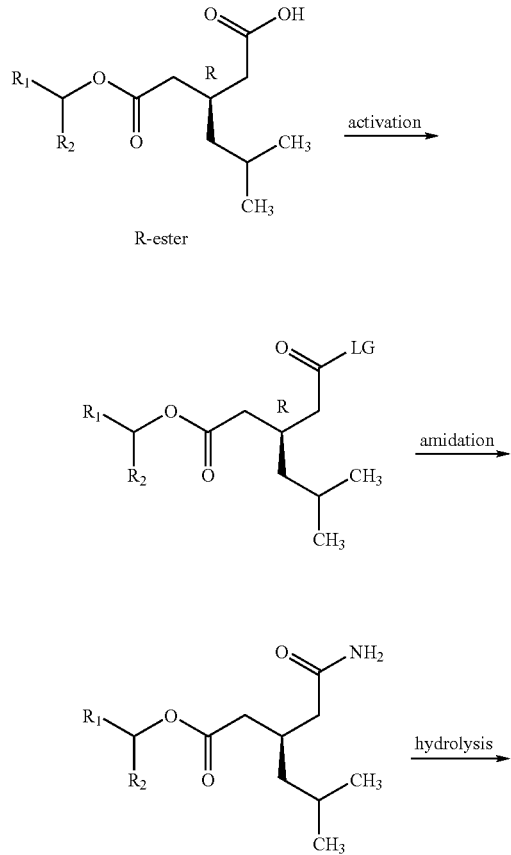

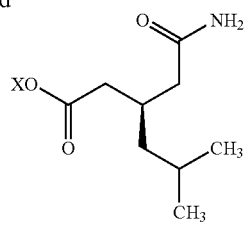

R-CMH or salt thereof wherein $R_1$ and $R_2$ are independently selected from the group consisting of H, aliphatic, branched, or cyclic $C_{1-12}$ hydrocarbons, $C_{6-9}$ aromatic hydrocarbons, and $CO_2H$; LG is a leaving group, where the leaving group is derived from the acid activating agent; and X is either H or an alkali metal. Preferably, $R_1$ is $CO_2H$ or H; $R_2$ is H, a $C_{6-9}$ aromatic hydrocarbon, or an aliphatic or branched $C_{1-12}$ hydrocarbon; or $R_1$ and $R_2$ form together a cyclic $C_{1-12}$ hydrocarbon.

Preferably, the $C_{6-9}$ aromatic hydrocarbon is phenyl. Preferably, the aliphatic, or branched $C_{1-12}$ hydrocarbons is methyl. Preferably, the cyclic $C_{1-12}$ hydrocarbon is 1,3,3-trimethylbicyclo[2.2.1]heptane. Preferred combinations of $R_1$ and $R_2$ are $CO_2H$ and phenyl, H and H, H and Me, H and phenyl, respectively, or $R_1$ and $R_2$ form together 1,3,3-trimethylbicyclo[2.2.1]heptane of the formula

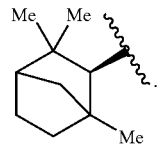

The ester moiety in the acid starting material can be chiral or non-chiral.

The starting R-ester can be provided by the above process using the chiral alcohol or the combination of the non-chiral alcohol and the chiral amine with the proviso that the opposite enantiomer of the chiral alcohol and of the chiral amine is used. The opposite enantiomer leads to the formation of the R-ester, rather than the S-ester as above.

Examples of suitable chiral alcohols include, but are not limited to, (R)-fenchyl alcohol, (R)-mandelic acid, and the opposite enantiomer of the following alcohols: benzylmandelate, ethylmandelate, methylmandelate, 1-phenylethanol, 1-phenyl-2-propanol, 1-phenyl-1-propanol, and trifluoromethyl-benzyl alcohol. Preferably, the chiral alcohol is either (R)-fenchyl alcohol or (R)-mandelic acid.

Preferably, the chiral amine is a chiral alkaloid. Preferably, the chiral alkaloid is a cinchona alkaloid. Examples for suitable cinchona alkaloids include, but are not limited to, quinine, cinchonidine and their dehydro derivatives. Preferably, the chiral amine is quinine of the following structure:

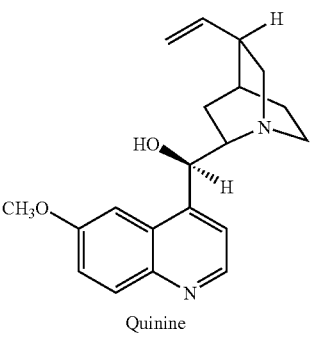

Quinine

The activation of the R-ester may be accomplished by combining the above R-ester, a base, and an acid activating agent in a solvent selected from a group consisting of $C_{6-10}$ aromatic hydrocarbons, $C_{3-5}$ ketones, $C_{2-5}$ ethers, $C_{2-7}$ esters, $C_{1-2}$ halogenated hydrocarbons, $C_{1-4}$ nitriles, and mixtures thereof to obtain an activated acid derivative of the formula

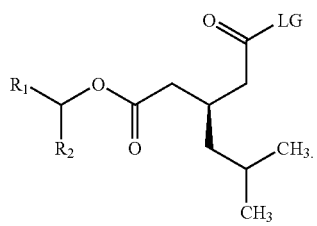

The base can be an organic base or an inorganic base. Preferably, the organic base is an aliphatic amine, and more preferably a $C_{2-12}$ aliphatic amine. Preferably, the $C_{2-12}$ aliphatic amine is selected from the group consisting of ethyl amine, diethyl amine, propyl amine dipropyl amine, butyl amine, tributylamine, diisopropyl amine, and triethylamine. Most preferably, the $C_{2-12}$ aliphatic amine is triethylamine.

Preferably, the inorganic base is an alkaline hydroxide, an alkaline carbonate or an alkaline bicarbonate. Preferably, the alkaline hydroxide is sodium hydroxide or potassium hydroxide. Preferably, the alkaline carbonate is either sodium carbonate or potassium carbonate. Preferably, the alkaline bicarbonate is either sodium bicarbonate or potassium bicarbonate. More preferably, the base is triethylamine.

Preferably, the $C_{6-10}$ aromatic hydrocarbon is a $C_{6-8}$ aromatic hydrocarbon, more preferably a $C_{6-7}$ aromatic hydrocarbon, and most preferably toluene. Preferably, the $C_{3-5}$ ketone is a $C_{3-4}$ ketone, more preferably a $C_3$ ketone, and most preferably acetone. A preferred $C_{2-5}$ ether is a $C_{4-5}$ ether and a more preferred $C_{2-5}$ ether is THF or MTBE. Preferably, the $C_{2-7}$ ester is a $C_{2-5}$ ester, more preferably a $C_{2-4}$ ester, and most preferably a $C_4$ ester. A particularly preferred $C_{2-7}$ ester is ethyl acetate. A preferred $C_{1-2}$ halogenated hydrocarbon is a $C_1$ halogenated hydrocarbon and a more preferred $C_{1-2}$ halogenated hydrocarbon is DCM. Preferably, the $C_{1-4}$ nitrile is a $C_{1-2}$ nitrile, more preferably a $C_2$ nitrile, and most preferably ACN. The most preferred solvent is DCM.

The term "acid activating agent" refers to a substance containing a group that activates a carbonyl group, i.e., makes the carbonyl group more susceptible to nucleophilic attack, when attached to it. Preferably, the acid activating agent is selected from a group consisting of: alkyl halo formates, anhydrides, and sulfonyl halides. Preferably, the alkyl halo formate is ethyl chloroformate or methyl chloroformate. Preferably, the anhydride is a symmetric or mixed anhydride, more preferably, acetic anhydride. Preferably, the sulfonyl halide is mesyl chloride or tosyl chloride. More preferably, the activating agent is ethyl chloroformate Typically, the solvent is combined with the starting R-ester and the base to obtain a mixture. The mixture is then cooled prior to the addition of the acid activating agent. Preferably, the mixture is cooled to a temperature of about 20° C. to about −5° C., and more preferably to about 5° C. to about 0° C.

After the acid activating agent is added to the mixture, the mixture is warmed. Preferably, the mixture is warmed to a temperature of about 10° C. to about 50° C., and more preferably, to about 20° C. to about 25° C. Preferably, the warmed mixture is maintained for about 1 to about 2 hours to obtain the activated acid derivative of the following formula:

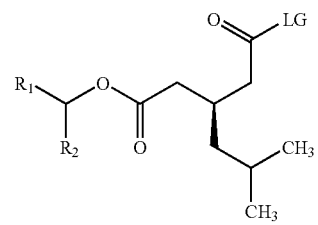

Preferably, $R_1$ and $R_2$ are H, and LG is $OCO_2Et$, providing an activated acid derivative of the following formula:

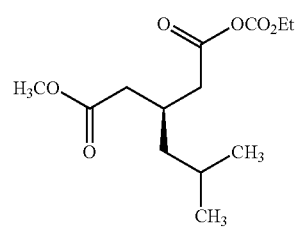

The activated acid derivative is then subjected to an amidation process that comprises combining the above activated acid derivative with ammonia, followed by addition of an acid or a base to obtain R-CMH. The reaction of the activated acid derivative with ammonia provides a slurry having the following amide.

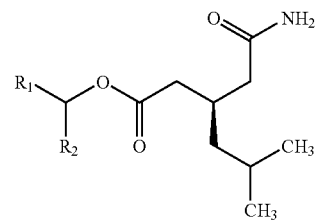

The ammonia can be provided as described above. Preferably, the ammonia is provided in the form of a gas.

The amide may be recovered from the slurry by any method known to one of ordinary skill in the art. Such methods include, but are not limited to, filtering the amide from the slurry, washing the amide, and drying the amide. Alternatively, the amide can be reacted with the acid or base without being isolated, i.e., in a one-pot reaction.

The ester group of the above amide is then hydrolyzed to R-CMH or a salt thereof by combining the amide with an acid or a base. When an acid is used, the above amide is hydrolyzed to R-CMH. When a base is used, the above amide is hydrolyzed to a salt of R-CMH. The salt of R-CMH can then be converted into R-CMH by adding an acid.

The acid can be an inorganic acid or an organic acid. Preferably, the inorganic acid is selected from the group consisting of HCl, HBr, $H_2SO_4$, and $H_3PO_4$, and more preferably HCl. Preferably, the organic acid is selected from the group consisting of acetic acid and formic acid. Most preferably, the acid is HCl.

The base is an inorganic base. Preferably, the base is an alkali metal base, thereby forming an alkali metal salt of R-CMH during the hydrolysis. Preferably the inorganic base is selected from the group consisting of NaOH, KOH and LiOH, and most preferably NaOH.

Preferably, the amide is combined with the acid or base to provide a mixture, which is stirred at a temperature of about 10° C. to about 50° C., and more preferably at about 20° C. to about 25° C. Preferably, the mixture is stirred for about 1 to about 10 hours, and more preferably for about 2 to about 8 hours, to obtain the R-CMH or salt thereof.

The R-CMH or salt thereof thus obtained may be recovered by any method known to one of ordinary skill in the art. Preferably, the R-CMH or salt thereof is recovered by adjusting the pH of the stirred mixture to about 1 to about 6, more preferably to about 2 to about 5, to provide a slurry; filtering the R-CMH or salt thereof from the slurry; washing the filtered R-CMH or salt thereof; and drying the R-CMH or salt thereof. Preferably, the pH is adjusted by adding a base to the mixture. Preferably, the base is an inorganic base and more preferably the base is selected from the group consisting of sodium hydroxide, potassium hydroxide, sodium carbonate, potassium carbonate, sodium bicarbonate, potassium bicarbonate. Optionally, an organic base, such as ammonia, can be used. Typically, the inorganic base can be used as a solid or as an aqueous solution.

The R-CMH or salt thereof prepared by any of the above-described processes may be converted to (S)-pregabalin. The conversion may be performed, for example, according to the processes disclosed in U.S. Patent application No. 2007/0073085, hereby incorporated by reference.

EXAMPLES

Asymmetric Ring Opening of IBG-Anhydride

Example 1

Preparation of Fenchyl Ester

A three-neck-flask (0.25 l) was charged with toluene (140 ml), Fenchyl alcohol (9.26 g) and NaH-60% (2.4 g). The mixture was heated to 80° C., and then cooled to 5° C. A solution of 3-isobutyl glutaric anhydride (6.8 g) in toluene (25 ml) was added to the mixture dropwise. The solution was stirred for 3 hours at room temperature. The solvent was evaporated to dryness to obtain the crude ester. The solid was dried at 55° C. under vacuum.

Example 2

Isolation of (S), (R)-Fenchyl Ester

The crude ester prepared in example 1, is added to a mixture of ethyl acetate and toluene, and heated to 80° C. (range 400 to 100° C.) until dissolution. The solution is cooled to 2° C. (range 0° to 20° C.) to get a yellowish solid of (S)-3-(1,3,3-trimethylbicyclo[2.2.1]heptan-2-yl)carbonyl)methyl)-5-methylhexanoic acid (Fenchyl ester), which is filtered from the mixture.

Example 3

Preparation and Isolation of (S), (R)-Mandelate Ester

A three-neck-flask (0.25 L) is charged with toluene (70 ml), S-mandelic acid (3.04 g) and NaH-60% (1.6 g). The mixture is heated to reflux and then cooled to room temperature. 3-isobutyl glutaric anhydride (3.4 g) is added drop-wise.

The solution is stirred for 6 hours at room temperature. The solvent is evaporated, and the residue is crystallized from ethyl acetate and toluene mixture to get an off-white solid of (S)-4-(((S)-carboxy(phenyl)methoxy)carbonyl)-3-isobutylbutanoic acid (Mandelate ester).

The solid is dried at 55° C. under vacuum.

Example 4

Asymmetric Ring Opening of IBG-Anhydride with Chiral Alkaloide

A three-neck-flask (0.25 L) is charged with quinidine (11 mmol), 3-isobutyl glutaric anhydride (10 mmol) and toluene (50 ml). The mixture is cooled at −55° C. Methanol (30 mmol) is added dropwise over a period of 10 min to the cooled suspension. The reaction is stirred at for 96 h. The solution is concentrated to dryness, and the resulting residue is dissolved in diethyl ether (65 ml). The solution is washed with HCl-2N, and the aqueous layer is back-extracted with ether. The combined organic layers are dried with $MgSO_4$, and filtered. The filtrate is evaporated to dryness.

Example 5

Asymmetric Ring Opening of IBG-Anhydride with Chiral Alkaloide

Methanol (6.2 ml, 153 mmol) was added to a flame-dried 250 ml single, round-bottomed flask equipped with magnetic stirrer and charged with Quinidine (7.14 g, 22 mmol), 3-isobutyl glutaric anhydride (3.28 g, 19.3 mmol) and Toluene (100 ml, 30.5 vol) at −75° C. The reaction was stirred for 21 hours. The solution was concentrated to dryness, and the resulting residue was dissolved in diethyl ether (125 ml). The solution was washed with HCl-2N (40 ml×3), and the aqueous layer was back-extracted with ether. The combined organic layers were evaporated until dryness, to give 3.56 g of a yellow oil of S-hemiester ((S)-3-((methoxycarbonyl)methyl)-5-methylhexanoic acid) (Optical purity 90%, Yield −91%).

Example 6

Asymmetric Ring Opening of IBG-Anhydride with Chiral Alkaloide

Methanol (6.2 ml, 153 mmol) was added to a 250 ml three-necked, round-bottomed flask equipped with magnetic stirrer and charged with Quinidine (7.14 g, 22 mmol), 3-isobutyl glutaric anhydride (3.28 g, 19.3 mmol) and Toluene (100 ml, 30.5 vol) at −50° C. The reaction was stirred for 2 hours. The slurry was washed with $H_2SO_4$-2N (40 ml×3). The organic layer was evaporated until dryness, to have 3.7 g yellow oil of S-Hemiester (Optical purity 90% Yield −95%).

Example 7

Asymmetric Ring Opening of IBG-Anhydride with Chiral Alkaloide

Methanol (6.2 ml, 153 mmol) was added to a 250 ml three-necked, round-bottomed flask equipped with magnetic stirrer and charged with Quinidine (12.5 g, 38.6 mmol), 3-isobutyl glutaric anhydride (3.28 g, 19.3 mmol) and Toluene (100 ml, 30.5 vol) at −78° C. The reaction was stirred for 22.5 hours. The slurry was washed with HCl-2N (40 ml×3). The organic layer was evaporated until dryness, to have 3.63 g yellow oil of S-Hemiester (Optical purity 90%, Yield −93%).

Example 8

Asymmetric Ring Opening of IBG-Anhydride with Chiral Alkaloide

Methanol (6.2 ml, 153 mmol) was added to a 250 ml three necked, round-bottomed flask equipped with magnetic stirrer and charged with Quinidine (7.14 g, 22 mmol), 3-isobutyl glutaric anhydride (3.28 g, 19.3 mmol) and Toluene (33 ml, 10 vol) at −78° C. The reaction was stirred for 19 hours. The solution was washed with HCl-2N (25 ml×3). The organic layer was evaporated until dryness, to give 3.38 g yellow oil of S-Hemiester (Optical purity 90%, Yield −87%).

Example 9

Asymmetric Ring Opening of IBG-Anhydride with Chiral Alkaloide

Methanol (6.2 ml, 153 mmol) was added to a 250 ml three-necked, round-bottomed flask equipped with magnetic stirrer and charged with Quinidine (7.14 g, 22 mmol), 3-isobutyl glutaric anhydride (3.28 g, 19.3 mmol) and Toluene (100 ml, 30 vol) at −78° C. The reaction was stirred for 2 hours. The slurry was washed with $H_2SO_4$-2N (40 ml×3). The organic layer was evaporated until dryness, to give 3.4 g yellow oil of S-Hemiester (Optical purity 95%, Yield −93%).

Example 10

Asymmetric Ring Opening of IBG-Anhydride with Chiral Alkaloide

To a stirred suspension of 3-isobutyl glutaric anhydride (88 mmol) and Quinidine (100 mmol) in Toluene (30 vol) at −50° C., Methanol (273 mmol) was added drop-wise. The reaction was stirred at −50° C. for 17 h. The solution was washed with $H_2SO_4$-2N. The organic layer was evaporated to dryness to obtain S-Hemiester. (Optical purity −94%, Yield −94%).

Example 11

Asymmetric Ring Opening of IBG-Anhydride with Chiral Alkaloide

To a stirred suspension of 3-isobutyl glutaric anhydride (19.3 mmol) and Quinidine (22 mmol) in Toluene (20 vol) at −50° C., Methanol (59.8 mmol) was added drop-wise. The reaction was stirred at −50° C. for 17 hours. The solution was washed with $H_2SO_4$-2N. The organic layer was evaporated to dryness to obtain S-Hemiester. (Optical purity −95%, Yield −89%).

Example 12

Asymmetric Ring Opening of IBG-Anhydride with Chiral Alkaloide

To a stirred suspension of 3-isobutyl glutaric anhydride (19.3 mmol) and Quinidine (22 mmol) in Toluene (10 vol) at −50° C., Methanol (59.8 mmol) was added drop-wise. The reaction was stirred at −50° C. for 4 hours. The solution was washed with $H_2SO_4$-2N. The organic layer was evaporated to dryness to obtain S-Hemiester. (Optical purity −94%, Yield −92%).

Example 13

Asymmetric Ring Opening of IBG-Anhydride with Chiral Alkaloide

To a stirred suspension of 3-isobutyl glutaric anhydride (19.3 mmol) and Quinidine (22 mmol) in Toluene (30 vol) at −50° C., Methanol (193 mmol) was added drop-wise. The reaction was stirred at −50° C. for 16 hours. The solution was washed with $H_2SO_4$-2N. The organic layer was evaporated to dryness to obtain S-Hemiester. (Optical purity −95%, Yield −83%).

Example 14

Asymmetric Ring Opening of IBG-Anhydride with Chiral Alkaloide

To a stirred suspension of 3-isobutyl glutaric anhydride (19.3 mmol) and Quinidine (22 mmol) in Toluene (10 vol) at −50° C., Methanol (59.8 mmol) was added drop-wise. The reaction was stirred at −50° C. for 22 hours. The solution was washed with $H_2SO_4$-2N. The organic layer was evaporated to dryness to obtain S-Hemiester. (Optical purity −91%, Yield −92%).

Example 15

Asymmetric Ring Opening of IBG-Anhydride with Chiral Alkaloide

To a stirred suspension of 3-isobutyl glutaric anhydride (270 mmol) and Quinidine (308 mmol) in Toluene (10 vol) at −50° C., Methanol (837 mmol) was added drop-wise. The reaction was stirred at −50° C. for 3 hours. The solution was washed with $H_2SO_4$-2N. The organic layer was evaporated to dryness obtain S-Hemiester. (Optical purity −95%, Yield −84%).

Example 16

Asymmetric Ring Opening of IBG-Anhydride with Chiral Alkaloide

To a stirred suspension of 3-isobutyl glutaric anhydride (19.3 mmol) and Cinchonine (22 mmol) in Toluene (30 vol) at −50° C., Methanol (59.8 mmol) was added drop-wise. The reaction was stirred at −50° C. for 15 hours. The solution was washed with $H_2SO_4$-2N. The organic layer was evaporated to dryness obtain S-Hemiester. (Optical purity −78%, Yield −99%).

Example 17

Asymmetric Ring Opening of IBG-Anhydride with Chiral Alkaloide

To a stirred suspension of 3-isobutyl glutaric anhydride (19.3 mmol) and Cinchonidine (22 mmol) in Toluene (30 vol) at −50° C., Methanol (59.8 mmol) was added drop-wise. The reaction was stirred at −50° C. for 15 hours. The solution was washed with $H_2SO_4$-2N. The organic layer was evaporated to dryness obtain R-Hemiester. (Optical purity −68%, Yield −100%).

Example 18

Asymmetric Ring Opening of IBG-Anhydride with Chiral Alkaloide

To a stirred suspension of 3-isobutyl glutaric anhydride (19.3 mmol) and Cinchonine (22 mmol) in Toluene (30 vol) at −78° C., Methanol (59.8 mmol) was added drop-wise. The reaction was stirred at −50° C. for 19 hours. The solution was washed with $H_2SO_4$-2N. The organic layer was evaporated to dryness obtain S-Hemiester. (Optical purity −74%, Yield −90%).

Example 19

Asymmetric Ring Opening of IBG-Anhydride with Chiral Alkaloide

Methanol (6.2 ml, 153 mmol) was added drop-wise to a 250 ml three-necked, round-bottomed flask equipped with magnetic stirrer and charged with Quinine (7.14 g, 22 mmol), 3-isobutyl glutaric anhydride (3.28 g, 19.3 mmol) and Toluene (100 ml, 30 vol) at −70° C. The reaction was stirred for 17 hours. The solution was concentrated to dryness, and the resulting residue was dissolved in diethyl ether (125 ml). The solution was washed with HCl-2N (40 ml×3). The organic layer was evaporated until dryness, to have 3.7 g yellow oil of R-Hemiester (Optical purity 80%, Yield −95%).

Amidation

Example 20

A three-neck-flask (0.25 l) is charged with aqueous $NH_3$ (40 ml) and the S-Me hemiester (4 g). The mixture is heated to 80° C. under pressure (5 Atm) for 6 hours. The solution is cooled to room temperature, and HCl is added to obtain a pH of 1. The mixture is cooled to 0° C., R-CMH is filtered and dried at 55° C. under vacuum.

Example 21

A 50 ml three-neck-flask was charged with aqueous $NH_3$ 22% (25 ml, 8 vol.) and S-CMH-methyl ester (MS-1750, 3.16 g). The solution was stirred at room temperature for 92 hours. 37% of HCl was added to obtain a pH of 3. The white slurry was cooled to 0° C., R-CMH was filtered and dried at 55° C. under vacuum during 14 hours to obtain 3.65 g of white powder R-CMH. (Optical purity −90%, Yield −100%).

Example 22

An autoclave was charged with aqueous $NH_3$ 22% (25 ml, 12.5 vol.) and S-CMH-methyl ester (MS-1848, 2 g). The solution was stirred at 75° C. at 2 Atm for 7 hours. 37% of HCl was added to obtain a pH of 3. Ethyl acetate (200 ml) was added to the white slurry, and the precipitant remained in the aqueous phase. Water (20 ml) was added to obtain clear solutions (two phases). The two phases were separated after stirred vigorously for 10 minutes. The organic phase was evaporated until dryness to give 1.62 g of R-CMH. (Optical purity 80%, Yield −80%).

Example 23

A 100 ml three-neck-flask was charged with aqueous $NH_3$ 22% (25 ml, 12.5 vol.) and S-CMH-methyl ester (GE-11426, 2 g). The solution was stirred at 40° C. for 25 hours. 37% of HCl was added to obtain a pH=3. The white slurry was vacuum filtered and the filter cake washed with water (5 ml). The white precipitate was dried at 55° C. under vacuum for 17 hours to obtain 2.45 g of white powder R-CMH. (Optical purity −87%, Yield −100%).

Example 24

An autoclave (0.1 L) was charged with aqueous $NH_3$ (25 ml) and S-Methyl-ester (2 g). The mixture was heated to 70° C. under pressure (1.5 bar) for 8 hours. The solution was cooled to room temperature, and 37% HCl was added to obtain pH 3. $NH_4Cl$ (1.8 g) was added to induce precipitation of the R-CMH. The precipitated R-CMH was filtered and dried at 55° C. under vacuum. (Optical purity −84%, Yield −60%).

Example 25

An autoclave (0.1 L) was charged with aqueous $NH_3$ (60 ml) and S-Methyl-ester (10 g). The mixture was heated to 70° C. under pressure (1.5 bar) for 25 hours. The solution was cooled to room temperature, and 37% HCl was added to obtain pH 3. $NH_4Cl$ (1.8 g) was added was added to induce precipitation of the R-CMH. The precipitated R-CMH was filtered and dried at 55° C. under vacuum. (Yield −100%).

Example 26

A solution of S-methyl-ester (20 mmol, GE-1381) in toluene (10 vol) was extracted with $NH_4OH$ 30% (2.6 vol×2) and stirred at room temperature as clear solution for 16 hours. $NH_4OH$ 30% (5.2 vol) was added to the solution and stirred at room temperature for 72 hours. The solution was acidified to pH 3 with $H_2SO_4$ 75%, and evaporated until dryness. The residue was triturating in acetone (20 vol), the solids were filtered off, and the acetone evaporated until dryness. The resulting residue was slurried in water (20 vol) for 17 hours. The precipitate was vacuum filtered and dried in a vacuum oven at 55° C. for 20 hours.

Example 27

A one-neck-flask (0.1 L) was charged with aqueous $NH_3$ (18 ml), the S-ester (3 g) and ammonium chloride (0.8 g, 1 eq). The solution was heated to 40° C. and stirred at this temperature for 24 hours and at room temperature for 18.5 hours. The solution was evaporated until dryness. Distilled water (15 vol.) was added and HCl was added to obtain pH of 4. The mixture was stirred for over night; R-CMH was filtered and dried at 55° C. under vacuum.

Example 28

One Pot Synthesis of R-CMH

To a stirred suspension of 3-isobutyl glutaric anhydride (118 mmol) and Quinidine (134 mmol) in Toluene (10 vol) at −50° C., Methanol (365 mmol) was added drop-wise. The reaction was stirred at −50° C. for 17 hours. The solution was washed with $H_2SO_4$-2N. The organic layer was filtered and extracted to $NH_4OH$ (aq.) 25% (10 vol). The aqueous solution was stirred in a closed flask at 40° C. for 24 hours and at room temperature for 48 hours. 37% HCl was added to obtain pH 3. The slurry was stirred 20 hours at room temperature and cooled to 5° C. R-CMH was filtered and dried at 55° C. under vacuum.

Example 29

Preparation of (S)-methyl 3-(carbamoylmethyl)-5-methylhexanoate

A round-bottomed flask is equipped with magnetic stirrer and charged with methylene dichloride (100 ml), (S)-3-((Methoxycarbonyl)methyl)-5-methylhexanoic acid (20 g) and with triethylamine (0.77 g) and cooled to 0-5° C. followed by addition of ethyl chloroformate (9 g). The mixture was stirred for 1-2 h at a temperature of 20° C. to 25° C., followed by quenching with 25% aqueous ammonia (100 ml). The resulted slurry is filtered and washed with water and dried to obtain a solid of (R)-methyl 3-(carbamoylmethyl)-5-methylhexanoate.

Example 30

Preparation of (R)-(+)-3-(carbamoylmethyl)-5-methylhexanoic acid (R-CMH)

A flask is equipped with a magnetic stirrer and is charged with 3N HCl (100 ml) and (R)-methyl 3-(carbamoylmethyl)-5-methylhexanoate (20 g). The mixture is stirred for 1-10 hours at a temperature of 20° C. to 25° C., followed by quenching with 47% NaOH to pH 3. The resulting slurry is filtered, washed with water, and dried to obtain a white solid of (R)-3-(carbamoylmethyl)-5-methylhexanoic acid.

Example 31

Conversion of (R)-CMH to (S)-Pregabalin

Example 12 from U.S. Publication No. 2007/0073085

A reactor (0.5 L) was loaded with water (165 ml) and NaOH (35.5 g) to obtain a solution. The solution was cooled to 15° C. and (R)-CMH (33 g) was added. $Br_2$ (28.51 g) was added dropwise (15 min) while keeping the temperature below 25° C. The mixture was heated to 60° C. for 15 min and then cooled to 15° C. Iso-butanol was added (100 ml) and then a solution of $H_2SO_4$ (66%) (33 ml) was added. The phases were separated, and the aqueous phase was extracted with Iso-butanol (83 ml). To the combined organic phases $Bu_3N$ (34.2 g) was added and the mixture was cooled to 2° C., and stirred for 2 hours. The solid was filtered, washed and dried at 55° C. under vacuum, providing (S)-PREGABALIN with total purity 99.86% area by HPLC.

Example 32

Conversion of (R)-CMH Sodium Salt to (S)-Pregabalin

A reactor is loaded with water and NaOH to obtain a solution. The solution is cooled to about 15° C. and (R)-CMH sodium salt is added. $Br_2$ is added dropwise to the reactor over a period of about 15 minutes, while keeping the temperature below about 25° C. The resulting mixture is heated to about 60° C. for about 15 min and then cooled to about 15° C. Iso-butanol is added and then a solution of $H_2SO_4$ (66%) is added to form a two-phase mixture. The two phases are separated, and the aqueous phase is extracted with iso-butanol. To the combined organic phases is added $Bu_3N$ and the mixture is cooled to about 2° C., and stirred for about 2 hours. The resulting solid is filtered, washed and dried at 55° C. under vacuum to provide (S)-pregabalin.

We claim:

1. A process for preparing (R)-(+)-3-(carbamoylmethyl)-5-methylhexanoic acid or a salt thereof having the formula

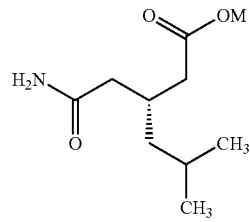

comprising:
   a) asymmetrically ring opening 3-isobutylglutaric anhydride to obtain a chiral ester having the formula:

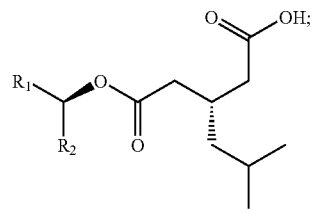

b) amidating the chiral ester to obtain a (R)-(+)-3-(carbamoylmethyl)-5-methylhexanoic acid salt having the formula

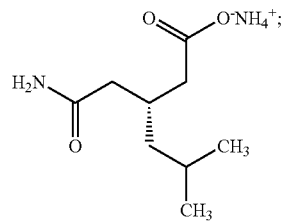

and, optionally,
   c) converting the (R)-(+)-3-(carbamoylmethyl)-5-methylhexanoic acid salt to (R)-(+)-3-(carbamoylmethyl)-5-methylhexanoic acid,
   wherein $R_1$ and $R_2$ are independently selected from the group consisting of: H, aliphatic, branched or cyclic $C_1$ to $C_{12}$ hydrocarbyl, $C_6$ to $C_9$ aromatic hydrocarbyl and $CO_2H$, and M is either H or $NH_4^+$.

2. The process of claim 1, wherein the $C_{6-9}$ aromatic hydrocarbon is benzyl, the aliphatic or branched $C_{1-12}$ hydrocarbon is methyl, and the cyclic $C_{1-12}$ hydrocarbon is 1,3,3-trimethylbicyclo[2.2.1]heptane.

3. The process of claim 1, wherein the combinations of $R_1$ and $R_2$ are $CO_2H$ and benzyl, H and H, H and Me, H and benzyl, respectively, or $R_1$ and $R_2$ form together 1,3,3-trimethylbicyclo[2.2.1]heptane.

4. The process of claim 1, wherein the ring opening is performed by combining 3-isobutylglutaric anhydride and a chiral alcohol.

5. The process of claim 1, wherein the ring opening is performed by combining 3-isobutylglutaric anhydride, a non-chiral alcohol, and a chiral amine.

6. A process for preparing (S)-pregabalin comprising:
   a) preparing R-(+)-3-(carbamoylmethyl)-5-methylhexanoic acid or a salt thereof by the process of claim 1; and
   b) converting the R-(+)-3-(carbamoylmethyl)-5-methylhexanoic acid or salt thereof into (S)-pregabalin.

7. A process for preparing R-(+)-3-(carbamoylmethyl)-5-methylhexanoic acid or a salt thereof having the formula

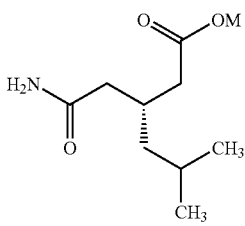

comprising:
   a) combining 3-isobutylglutaric anhydride, a chiral alcohol, a solvent selected from the group consisting of $C_{6-10}$ aromatic hydrocarbons, $C_{3-5}$ ketones, $C_{2-5}$ ethers, $C_{2-7}$ esters, $C_{1-2}$ halogenated hydrocarbons, and $C_{1-4}$ nitriles, and a base to obtain a chiral ester of the formula

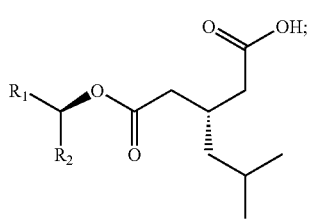

b) mixing with ammonia to obtain a (R)-(+)-3-(carbamoylmethyl)-5-methylhexanoic acid salt having the formula

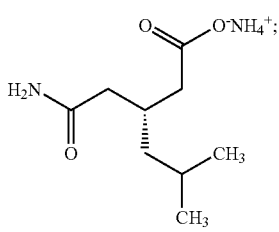

and, optionally,
   c) adding an acid to obtain R-(+)-3-(carbamoylmethyl)-5-methylhexanoic acid,
   wherein $R_1$ and $R_2$ are independently selected from the group consisting of H, aliphatic, branched, or cyclic $C_{1-12}$ hydrocarbons, $C_{6-9}$ aromatic hydrocarbons, and $CO_2H$; and M is either H or $NH_4^+$.

8. The process of claim 7, wherein the base is selected from the group consisting of sodium hydride and butyl lithium.

9. The process of claim 7, wherein the chiral alcohol is selected from the group consisting of (S)-fenchyl alcohol, (S)-mandelic acid, benzylmandelate, ethylmandelate, methylmandelate, 1-phenylethanol, 1-phenyl-2-propanol, 1-phenyl-1-propanol, and trifluoromethyl-benzyl alcohol.

10. The process of claim 7, wherein the chiral alcohol is (S)-fenchyl alcohol or (S)-mandelic acid.

11. The process of claim 7, wherein the solvent is selected from the group consisting of $C_{6-8}$ aromatic hydrocarbons, $C_{3-4}$ ketones, $C_{4-5}$ ethers, $C_{2-5}$ esters, $C_1$ halogenated hydrocarbons, and $C_{1-2}$ nitriles.

12. The process of claim 7, wherein the solvent is selected from the group consisting of toluene, acetone, tetrahydrofuran, methyl tert-butyl ether, ethyl acetate, dichloromethane, and acetonitrile.

13. The process of claim 7, wherein the solvent and the chiral alcohol are combined to form a mixture, and the base and the 3-isobutylglutaric anhydride are added to the mixture in succession.

14. The process of claim 13, wherein the base is added to the mixture at a temperature of about −78° C. to about 110° C.

15. The process of claim 7, wherein the combination of step a) is maintained at a temperature of about 0° C. to about 50° C. to obtain the chiral ester.

16. The process of claim 7, wherein the chiral ester is crystallized prior to mixing with the ammonia.

17. The process of claim 16, wherein the chiral ester is crystallized from a solvent selected from the group consisting of $C_{6-10}$ aromatic hydrocarbons, $C_{3-5}$ ketones, $C_{2-5}$ ethers, $C_{2-7}$ esters, $C_{1-2}$ halogenated hydrocarbons, $C_{1-4}$ nitriles, and mixtures thereof.

18. The process of claim 16, wherein the chiral ester is crystallized from a mixture of toluene and ethyl acetate.

19. The process of claim 7, wherein the ammonia is provided in the form of a solution.

20. The process of claim 19, wherein the ammonia is in solution in a solvent selected from the group consisting of water, an organic solvent, or mixtures of water and organic solvent.

21. The process of claim 19, wherein the solution of ammonia is provided by any one of the following methods: a) bubbling ammonia gas into the solvent; b) adding ammonium chloride to the mixture obtained in step b); or c) a combination of a) and b).

22. The process of claim 7, wherein the mixture of step b) is maintained at a temperature of about −40° C. to about 110° C. to obtain the (R)-(+)-3-(carbamoylmethyl)-5-methylhexanoic acid salt.

23. The process of claim 7, wherein the mixture of step b) is maintained at a pressure of about 1 to about 6 atmospheres to obtain the (R)-(+)-3-(carbamoylmethyl)-5-methylhexanoic acid salt.

24. The process of claim 7, wherein the acid is selected from the group consisting of HCl, HBr, $H_2SO_4$, $H_3PO_4$, acetic acid, and formic acid.

25. The process of claim 7, wherein the acid is present in an amount sufficient to obtain a pH of about 0 to about 5.

26. The process of claim 7, wherein step c) further comprises cooling to a temperature of about 10° C. to about −5° C. to precipitate the R-(+)-3-(carbamoylmethyl)-5-methylhexanoic acid.

27. A process for preparing (S)-pregabalin comprising:
   a) preparing R-(+)-3-(carbamoylmethyl)-5-methylhexanoic acid or a salt thereof by the process of claim 7; and
   b) converting the R-(+)-3-(carbamoylmethyl)-5-methylhexanoic acid or salt thereof into (S)-pregabalin.

28. A process for preparing R-(+)-3-(carbamoylmethyl)-5-methylhexanoic acid or a salt thereof having the formula

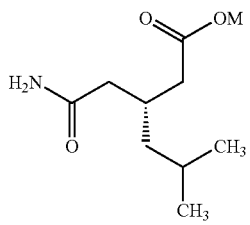

comprising:
a) combining 3-isobutylglutaric anhydride, a non-chiral alcohol, a chiral amine, and a solvent selected from the group consisting of $C_{6-10}$ aromatic hydrocarbons, $C_{2-5}$ ethers, $C_{1-2}$ halogenated hydrocarbons, and mixtures thereof to obtain a chiral ester having the formula

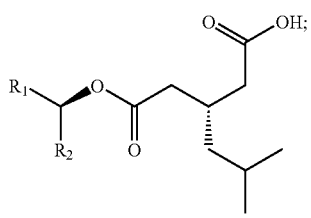

b) mixing with ammonia to obtain a (R)-(+)-3-(carbamoylmethyl)-5-methylhexanoic acid salt having the formula

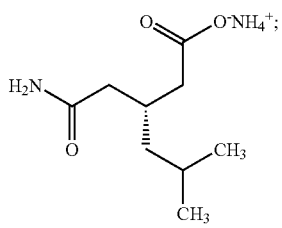

and, optionally,
c) adding an acid to obtain R-(+)-3-(carbamoylmethyl)-5-methylhexanoic acid,
wherein $R_1$ and $R_2$ are independently selected from the group consisting of H, aliphatic, branched, or cyclic $C_{1-12}$ hydrocarbons, $C_{6-9}$ aromatic hydrocarbons, and $CO_2H$; and M is either H or $NH_4^+$.

29. The process of claim 28, wherein the solvent is selected from the group consisting of $C_{6-8}$ aromatic hydrocarbons, $C_{4-5}$ ethers, and $C_1$ halogenated hydrocarbons.

30. The process of claim 28, wherein the solvent is selected from the group consisting of toluene, tetrahydrofuran, and dichloromethane.

31. The process of claim 28, wherein the chiral amine is a chiral alkaloid.

32. The process of claim 31, wherein the chiral alkaloid is a cinchona alkaloid.

33. The process of claim 32, wherein the cinchona alkaloid is selected from the group consisting of quinidine, cinchonine and their dehydro derivatives.

34. The process of claim 32, wherein the cinchona alkaloid is quinidine.

35. The process of claim 28, wherein the non-chiral alcohol is a $C_{1-7}$ alcohol.

36. The process of claim 28, wherein the non-chiral alcohol is methanol, ethanol, propanol, n-butanol, or benzyl alcohol.

37. The process of claim 28, wherein the non-chiral alcohol is added to a suspension of the 3-isobutylglutaric anhydride, the chiral amine, and the solvent.

38. The process of claim 37, wherein the non-chiral alcohol is added to the suspension at a temperature of about 20° C. to about −78° C.

39. The process of claim 28, wherein the chiral ester is crystallized prior to mixing with the ammonia.

40. The process of claim 39, wherein the chiral ester is crystallized from a solvent selected from the group consisting of $C_{6-10}$ aromatic hydrocarbons, $C_{3-5}$ ketones, $C_{2-5}$ ethers, $C_{2-7}$ esters, $C_{1-2}$ halogenated hydrocarbons, $C_{1-4}$ nitriles, and mixtures thereof.

41. The process of claim 39, wherein the chiral ester is crystallized from a mixture of toluene and ethyl acetate.

42. The process of claim 40, wherein the crystallization comprises combining the chiral ester and the solvent; heating the combination to a temperature of about 40° C. to about 150° C. to form a solution; and cooling the solution to a temperature of about 30° C. to about 0° C. to precipitate the chiral ester.

43. The process of claim 28, wherein the ammonia is provided in the form of a solution.

44. The process of claim 43, wherein the ammonia is in solution in a solvent selected from the group consisting of water, an organic solvent, or mixtures of water and organic solvent.

45. The process of claim 44, wherein the solution of ammonia is provided by any one of the following methods: a) bubbling ammonia gas into the solvent; b) adding ammonium chloride to the mixture obtained in step b); or c) a combination of a) and b).

46. The process of claim 28, wherein the mixture of step b) is maintained at a temperature of about −40° C. to about 110° C. to obtain the (R)-(+)-3-(carbamoylmethyl)-5-methylhexanoic acid salt.

47. The process of claim 28, wherein the mixture of step b) is maintained at a pressure of about 1 to about 6 atmospheres to obtain the (R)-(+)-3-(carbamoylmethyl)-5-methylhexanoic acid salt.

48. The process of claim 28, wherein the acid is selected from the group consisting of HCl, HBr, $H_2SO_4$, $H_3PO_4$, acetic acid, and formic acid.

49. The process of claim 28, wherein the acid is present in an amount sufficient to obtain a pH of about 0 to about 5.

50. The process of claim 28, wherein step c) further comprises cooling to a temperature of about 10° C. to about −5° C. to precipitate the R-(+)-3-(carbamoylmethyl)-5-methylhexanoic acid.

51. A process for preparing (S)-pregabalin comprising:
a) preparing R-(+)-3-(carbamoylmethyl)-5-methylhexanoic acid or a salt thereof by the process of claim 28; and
b) converting the R-(+)-3-(carbamoylmethyl)-5-methylhexanoic acid or salt thereof into (S)-pregabalin.

52. A process for preparing R-(+)-3-(carbamoylmethyl)-5-methylhexanoic acid or a salt thereof having the formula

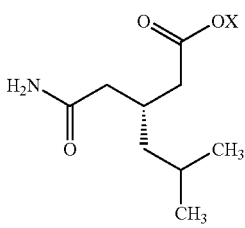

comprising:
a) combining a chiral ester having the formula

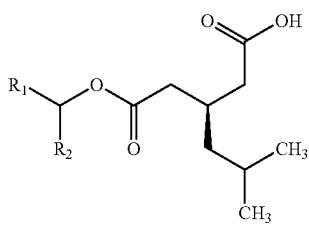

with an acid activating agent and a base to obtain an activated acid derivative having the formula

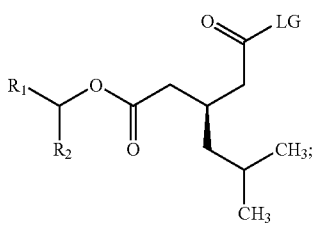

b) amidating the activated acid derivative to obtain a carbamoyl ester having the formula

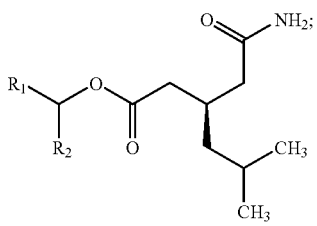

c) hydrolyzing the carbamoyl ester with an acid or a base to obtain R-(+)-3-(carbamoylmethyl)-5-methylhexanoic acid or a salt thereof, respectively; and, optionally,
d) converting the salt of R-(+)-3-(carbamoylmethyl)-5-methylhexanoic acid into R-(+)-3-(carbamoylmethyl)-5-methylhexanoic acid, wherein $R_1$ and $R_2$ are independently selected from the group consisting of H, aliphatic, branched, or cyclic $C_{1-12}$ hydrocarbons, $C_{6-9}$ aromatic hydrocarbons, and $CO_2H$; and LG is a leaving group; where the leaving group is derived from the acid activating agent; and wherein X is H or an alkali metal.

53. The process of claim 52, wherein the $C_{6-9}$ aromatic hydrocarbon is benzyl, the aliphatic or branched $C_{1-12}$ hydrocarbon is methyl, and the cyclic $C_{1-12}$ hydrocarbon is 1,3,3-trimethylbicyclo[2.2.1]heptane.

54. The process of claim 52, wherein the combinations of $R_1$ and $R_2$ are $CO_2H$ and benzyl, H and H, H and Me, H and benzyl, respectively, or $R_1$ and $R_2$ form together 1,3,3-trimethylbicyclo[2.2.1]heptane.

55. The process of claim 52, wherein the chiral ester is prepared by:
a) combining 3-isobutylglutaric anhydride, a chiral alcohol, a solvent selected from the group consisting of $C_{6-10}$ aromatic hydrocarbons, $C_{3-5}$ ketones, $C_{2-5}$ ethers, $C_{2-7}$ esters, $C_{1-2}$ halogenated hydrocarbons, and $C_{1-4}$ nitriles, and an inorganic base; or
b) combining 3-isobutylglutaric anhydride, a non-chiral alcohol, a chiral amine, and a solvent selected from the group consisting of $C_{6-10}$ aromatic hydrocarbons, $C_{2-5}$ ethers, $C_{1-2}$ halogenated hydrocarbons, and mixtures thereof.

56. The process of claim 55, wherein the chiral alcohol is selected from the group consisting of (R)-fenchyl alcohol, (R)-mandelic acid, benzylmandelate, ethylmandelate, methylmandelate, 1-phenylethanol, 1-phenyl-2-propanol, 1-phenyl-1-propanol, and trifluoromethyl-benzyl alcohol.

57. The process of claim 55, wherein the chiral alcohol is (R)-fenchyl alcohol or (R)-mandelic acid.

58. The process of claim 55, wherein the chiral amine is a chiral alkaloid.

59. The process of claim 58, wherein the chiral alkaloid is a cinchona alkaloid.

60. The process of claim 59, wherein the cinchona alkaloid is selected from the group consisting of quinine, cinchonidine and their dehydro derivatives.

61. The process of claim 59, wherein the cinchona alkaloid is quinine.

62. The process of claim 52, wherein the base of step a) is an aliphatic amine, an alkaline hydroxide, an alkaline carbonate, or an alkaline bicarbonate.

63. The process of claim 52, wherein the base of step a) is ethyl amine, diethyl amine, propyl amine, dipropyl amine, butyl amine, tributylamine, diisopropyl amine, triethylamine, sodium hydroxide, potassium hydroxide, sodium carbonate, potassium carbonate, sodium bicarbonate, or potassium bicarbonate.

64. The process of claim 52, wherein the chiral ester, the acid activating agent, and the base are combined in the presence of a solvent selected from a group consisting of $C_{6-10}$ aromatic hydrocarbons, $C_{3-5}$ ketones, $C_{2-5}$ ethers, $C_{2-7}$ esters, $C_{1-2}$ halogenated hydrocarbons, $C_{1-4}$ nitriles, and mixtures thereof.

65. The process of claim 64, wherein the solvent is selected from the group consisting of $C_{6-8}$ aromatic hydrocarbons, $C_{3-4}$ ketones, $C_{4-5}$ ethers, $C_{2-5}$ esters, $C_1$ halogenated hydrocarbons, and $C_{1-2}$ nitriles.

66. The process of claim 64, wherein the solvent is selected from the group consisting of toluene, acetone, tetrahydrofuran, methyl tert-butyl ether, ethyl acetate, dichloromethane, and acetonitrile.

67. The process of claim 64, wherein the solvent is combined with the chiral ester and the base to obtain a mixture, and the acid activating agent is added to the mixture.

68. The process of claim 67, wherein the mixture of solvent, acid, and base is cooled to a temperature of about 20° C. to about −5° C. prior to the addition of the acid activating agent.

69. The process of claim 68, wherein, after the addition of the acid activating agent, the mixture is warmed to a temperature of about 10° C. to about 50° C.

70. The process of claim 52, wherein the acid activating agent is selected from the group consisting of alkyl halo formates, anhydrides, and sulfonyl halides.

71. The process of claim 52, wherein the acid activating agent is ethyl chloroformate, methyl chloroformate, acetic anhydride, mesyl chloride, or tosyl chloride.

72. The process of claim 52, wherein $R_1$ and $R_2$ are H, and LG is $OCO_2Et$.

73. The process of claim 52, wherein the activated acid derivative is amidated by mixing with ammonia.

74. The process of claim 73, wherein the ammonia is provided in the form of a solution.

75. The process of claim 74, wherein the ammonia is in solution in a solvent selected from the group consisting of water, an organic solvent, or mixtures of water and organic solvent.

76. The process of claim 74, wherein the solution of ammonia is provided by any one of the following methods: a) bubbling ammonia gas into the solvent; b) adding ammonium chloride to the mixture obtained in step b); or c) a combination of a) and b) bubbling ammonia gas into the solvent or by adding ammonium chloride to the mixture obtained in step b).

77. The process of claim 52, wherein the acid is selected from the group consisting of HCl, HBr, $H_2SO_4$, $H_3PO_4$, acetic acid, or formic acid.

78. The process of claim 52, wherein the base of step c) is an inorganic base.

79. The process of claim 78, wherein the inorganic base is selected from the group consisting of NaOH, KOH and LiOH.

80. The process of claim 52, wherein step c) further comprises stirring at a temperature of about 10° C. to about 50° C.

81. A process for preparing (S)-pregabalin comprising:
  a) preparing R-(+)-3-(carbamoylmethyl)-5-methylhexanoic acid or a salt thereof by the process of claim 52; and
  b) converting the R-(+)-3-(carbamoylmethyl)-5-methylhexanoic acid or salt thereof into (S)-pregabalin.

* * * * *